_(12)_ United States Patent
Kim et al.

(10) Patent No.: US 8,886,278 B2
(45) Date of Patent: Nov. 11, 2014

(54) OPTICAL STIMULUS PROBE WITH REFLECTING SURFACE

(75) Inventors: JinSeok Kim, Seoul (KR); Eui-Sung Yoon, Seoul (KR); Hyun-Joon Shin, Seoul (KR); Jun-Kyo Francis Suh, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 235 days.

(21) Appl. No.: 13/175,236

(22) Filed: Jul. 1, 2011

(65) Prior Publication Data

US 2012/0101356 A1    Apr. 26, 2012

(30) Foreign Application Priority Data

Oct. 26, 2010 (KR) .......................... 10-2010-0104376

(51) Int. Cl.
*A61B 5/04* (2006.01)
*A61N 1/04* (2006.01)
*A61B 5/0484* (2006.01)
*A61B 5/00* (2006.01)

(52) U.S. Cl.
CPC ............ *A61B 5/04842* (2013.01); *A61B 5/0059* (2013.01)
USPC .............................. 600/373; 600/378; 607/92

(58) Field of Classification Search
USPC .................. 600/373, 377–379; 607/89, 92
See application file for complete search history.

(56) References Cited

U.S. PATENT DOCUMENTS

| 5,018,529 | A  | * | 5/1991  | Tenerz et al. ................. 600/480 |
|-----------|----|---|---------|----------------------------------------|
| 5,989,245 | A  | * | 11/1999 | Prescott ........................... 606/14 |
| 6,564,087 | B1 | * | 5/2003  | Pitris et al. .................... 600/478 |
| 6,819,958 | B2 | * | 11/2004 | Weiner et al. ................. 607/116 |
| 7,116,886 | B2 | * | 10/2006 | Colgan et al. ................. 385/137 |
| 7,883,536 | B1 | * | 2/2011  | Bendett et al. ................. 607/89 |
| 2008/0077200 | A1 | * | 3/2008  | Bendett et al. ................. 607/89 |
| 2010/0030043 | A1 | * | 2/2010  | Kuhn ........................... 600/339 |
| 2010/0268058 | A1 | * | 10/2010 | Chen ........................... 600/407 |
| 2011/0112591 | A1 | * | 5/2011  | Seymour et al. .................. 607/3 |
| 2011/0208032 | A1 | * | 8/2011  | Takiguchi et al. ............ 600/393 |
| 2011/0295347 | A1 | * | 12/2011 | Wells et al. .................... 607/89 |
| 2012/0172952 | A1 | * | 7/2012  | Yoon et al. ..................... 607/92 |
| 2013/0079615 | A1 | * | 3/2013  | Yoon et al. .................... 600/377 |

* cited by examiner

*Primary Examiner* — Lee S Cohen
*Assistant Examiner* — Erin M Cardinal
(74) *Attorney, Agent, or Firm* — Fenwick & West LLP

(57) ABSTRACT

An optical stimulation probe has a probe body inserted into a subject, an electrode formed on the probe body and collecting a response signal from the subject, a light irradiator attached to the probe body and irradiating an optical signal and a reflecting surface formed on the probe body on the path of the optical signal. The reflecting surface changes the course of the optical signal irradiated from the light irradiator to the direction where the electrode faces by reflecting the optical signal. The electrode may be formed on a side portion of the probe body such that it faces a direction perpendicular to a length direction of the probe body, and the optical signal reflected by the reflecting surface may travel along a direction perpendicular to the length direction of the probe body, such that the direction where the electrode faces and the direction along which the reflected optical signal travels are parallel to each other.

5 Claims, 1 Drawing Sheet

OPTICAL STIMULUS PROBE WITH REFLECTING SURFACE

CROSS-REFERENCE TO RELATED APPLICATION

This application claims priority to Korean Patent Application No. 10-2010-0104376, filed on Oct. 26, 2010, and all the benefits accruing therefrom under 35 U.S.C. §119, the contents of which in its entirety are herein incorporated by reference.

BACKGROUND

1. Field

The present disclosure relates to an optical stimulation probe, more particularly to an optical stimulation probe with a reflecting surface for optically stimulating a subject and collecting signals in response thereto.

2. Description of the Related Art

Recently, studies are carried out actively on stimulation of the cranial nerves of a subject and detection and analysis of signals in response thereto, in order to treat brain diseases and understand the operation of the brain.

A neural probe that can be inserted into a subject is used to directly stimulate the cranial nerves of the subject and acquire information thereabout. Further, a microsized neural probe with an electrode array mounted thereon was developed to acquire as much information as possible resulting from the stimulation of the cranial nerves.

In general, an existing neural probe applies an electrical stimulus to the cranial nerves using electrodes assembled on the probe body so as to stimulate the cranial nerves. However, such electrical stimulation may damage the cranial nerves and, since the brain is composed of electrically conducting materials, it is impossible to apply a localized stimulus.

Thus, an optical stimulation probe capable of optically stimulating the cranial nerves using light and collecting response signals was introduced recently.

FIG. 1 schematically shows an existing optical stimulation probe 1.

As shown in FIG. 1, an existing optical stimulation probe 1 consists of a silicon probe body 2 to which an optical fiber 3 or an optical waveguide capable of transmitting light is attached. The optical stimulation probe 1 is inserted into a subject, e.g. a mouse.

On the probe body 2, an electrode 4 for collecting a response signal and an electrical conductor 5 electrical connected with the electrode 4 are provided.

An optical signal 6 generated from an external light source (not shown) is irradiated through the optical fiber 3 to stimulate a particular nerve 7, and a response signal 8 from the stimulated nerve 7 is collected by the electrode 4 for analysis of the neuronal activities.

In such an existing optical stimulation probe, since the path of the irradiated of the optical signal 6 is perpendicular to the electrode 4, the distance between the nerve 7 stimulated by the optical signal 6 from the electrode 4 is relatively long.

The cranial nerve signal has a small intensity and is easily amplified or attenuated due to noises. Considering that signals of better quality can be collected at the electrode when the distance from the electrode to the stimulated site is closer, it is needed to make the distance between the optically stimulated site and the electrode where the response signal from the stimulated site is collected as short as possible.

SUMMARY

The present disclosure is directed to providing an optical stimulation probe wherein an optical signal for applying an optical stimulus travels along a direction to which an electrode for collecting a response signal faces, thereby minimizing the distance between the site stimulated by the optical signal and the electrode and allowing to acquire a high-quality response signal information.

In one aspect, there is provided an optical stimulation probe including: a probe body inserted into a subject; an electrode formed on the probe body and collecting a response signal from the subject; a light irradiator attached to the probe body and irradiating an optical signal; and a reflecting surface formed on the probe body on the path of the optical signal, wherein the reflecting surface changes the course of the optical signal irradiated from the light irradiator to the direction where the electrode faces by reflecting the optical signal.

The electrode may be formed on a side portion of the probe body such that it faces a direction perpendicular to a length direction of the probe body, and the optical signal reflected by the reflecting surface may travel along a direction perpendicular to the length direction of the probe body, such that the direction where the electrode faces and the direction along which the reflected optical signal travels are parallel to each other.

A seating groove may be formed on the probe body along the length direction of the probe body. The light irradiator may be seated in the seating groove, and the seating groove may be provided with a slant surface facing an end portion of the light irradiator from which the optical signal is output. And, the reflecting surface may be the slant surface.

The probe body may be formed of silicon, and the seating groove may be formed by wet etching.

The probe body may be formed from a silicon wafer having a [1, 0, 0] lattice structure.

And, the light irradiator may be an optical fiber or an optical waveguide transmitting an optical signal generated by an external light source.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Exemplary embodiments now will be described more fully hereinafter with reference to the accompanying drawings, in which exemplary embodiments are shown. The present disclosure may, however, be embodied in many different forms and should not be construed as limited to the exemplary embodiments set forth therein. Rather, these exemplary embodiments are provided so that the present disclosure will be thorough and complete, and will fully convey the scope of the present disclosure to those skilled in the art. In the description, details of well-known features and techniques may be omitted to avoid unnecessarily obscuring the presented embodiments.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 1:
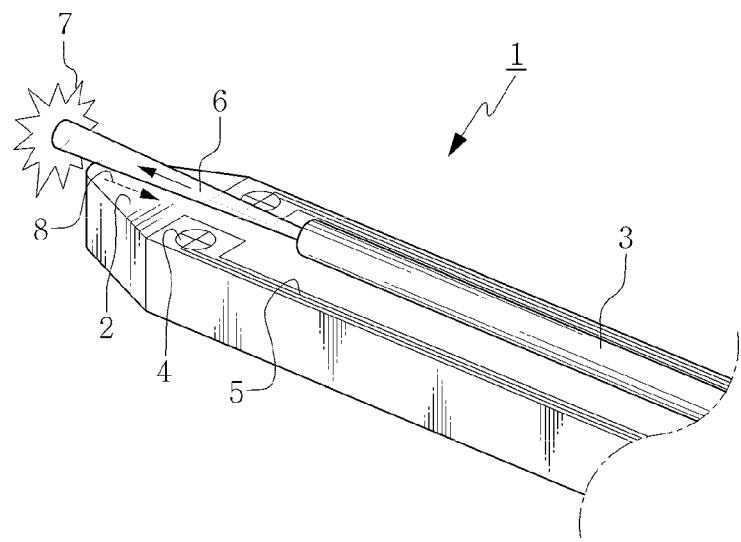
FIG. 1 schematically shows an existing optical stimulation probe.
Figure 2:
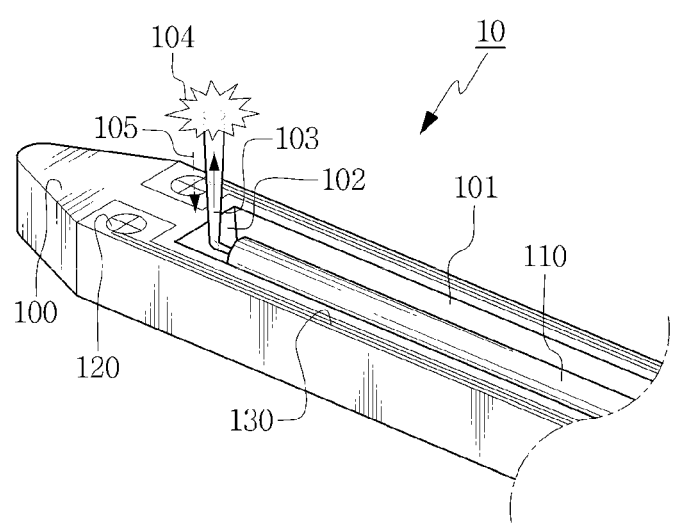
FIG. 2 schematically shows an optical stimulation probe according to the present disclosure.

FIG. 2 schematically shows an optical stimulation probe 10 according to the present disclosure.

Referring to FIG. 2, an optical stimulation probe 10 according to the present disclosure comprises a probe body 100, a light irradiator 110 attached to the probe body 100, and an electrode 120 formed on the probe body 100.

The probe body 100 is inserted into the body of a subject such as a mouse. Its front end portion is made sharp for easier insertion into the body of the subject.

The electrode 120 is provided on the front end portion of the probe body 100. The electrode 120 collects a response signal from an optically stimulated site.

An electrical conductor 130 is provided on the probe body 100. The electrical conductor 130 is electrically connected to the electrode 120 and transmits the signal collected by the electrode 120 to outside.

In an embodiment, an optical fiber 110 is used as the light irradiator for irradiating light. The optical fiber 110 irradiates light, i.e. an optical stimulation signal 103, generated by an external light source (not shown).

Although the optical fiber 110 is used as the light irradiator in this embodiment, the disclosure is not limited thereto. For example, an optical waveguide made of a light-transmitting material may be used as the light irradiator.

A seating groove 100 is formed on the probe body 100 along the length direction of the probe body 100. The seating groove 101 is formed to extend close to the electrode 120 as much as possible. The optical fiber 110 is seated in the seating groove 101.

As seen in FIG. 2, the seating groove 101 is provided with a slant surface 102 at an end portion thereof. When the optical fiber 110 is seated in the seating groove 101, the slant surface 102 faces an end portion of the optical fiber 110 from which the optical signal 103 is output, and is located on the path of the optical signal 103 irradiated from the optical fiber 110.

In an embodiment, the probe body 100 is formed from a silicon wafer having a [1, 0, 0] lattice structure, and the seating groove 101 is formed by wet etching.

When a silicon wafer having a [1, 0, 0] lattice structure is etched by wet etching, it is etched with a specific angle of 54.74° and the etched surface can reflect light.

Since the silicon wet etching is a simple and highly reliable process, the slant surface 102 formed by wet etching is useful as a reflecting surface for reflecting the optical signal. Accordingly, in this embodiment, the slant surface 102 is used as the reflecting surface for reflecting the optical signal 103.

The optical signal 103 generated by the external light source is irradiated to the reflecting surface 102 through the optical fiber 110. The irradiated optical signal 103 is reflected by the slant surface, i.e. the reflecting surface 102, and changes its course. As shown in FIG. 2, the reflected optical signal 103 travels along the direction where the electrode 120 faces.

As described earlier, since the reflecting surface 102 is etched with a specific angle of 54.74°, the optical signal 103 reflected by the reflecting surface 102 travels along a direction perpendicular to the length direction of the probe body 100, which is parallel to the direction where the electrode 120 faces.

The reflected optical signal 103 stimulates a nerve 104 located at the direction where the electrode 120 faces. Since the reflecting surface 102 is close to the electrode 120 as much as possible and the reflected optical signal 103 travels along the direction parallel to the direction where the electrode 120 faces, the nerve 104 closest to the electrode 120 is stimulated by the optical signal 103.

A response signal 105 from the stimulated nerve 104 is collected by the electrode 120. As shown in FIG. 2, the traveling path of the collected response signal 105 is substantially the same as the traveling path of the reflected optical signal 103.

As described, since the reflected optical signal 103 travels along the direction parallel to the direction where the electrode 120 faces and stimulates the nerve 104 which is closest to the electrode 120, the distance from the site stimulated by the optical signal 103 to the electrode 120 is minimized.

That is to say, the traveling distance of the response signal 105 from the site stimulated by the optical signal 103 to the electrode 120 is minimized. Accordingly, the possibility that the neuronal response signal is amplified or attenuated due to noises is decreased, and the signal sensitivity of the electrode 120 is improved significantly.

Since the seating groove 101 is formed on the probe body 100 and the optical fiber 110 is seated therein, the overall size of the optical stimulation probe 10 is decreased. Further, since the slant surface of the seating groove 101 is used as the reflecting surface, an additional process for forming the reflecting surface is unnecessary, resulting in simplified manufacturing process and apparatus structure.

However, the present disclosure is not limited to the use of the slant surface of the seating groove 101 as the reflecting surface for reflecting the optical signal. For example, a projecting portion may be formed on the probe body 100, and the projecting portion may be processed to form a slant surface capable of reflecting light for use as the reflecting surface. In this case, the optical fiber may be attached on the probe body using, for example, a hardener. Further, in case an optical waveguide is used as the light irradiator, the optical waveguide may be formed on the probe body through a microfabrication process.

With minimized distance between the optically stimulated site and the electrode which collects the response signal, the optical stimulation probe according to the present disclosure allows significant improvement of signal acquisition sensitivity of the electrode and thus provides a more accurate response signal information.

While the exemplary embodiments have been shown and described, it will be understood by those skilled in the art that various changes in form and details may be made thereto without departing from the spirit and scope of the present disclosure as defined by the appended claims.

In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. An optical stimulation probe comprising:
a probe body configured for insertion into a subject;
an electrode formed on the probe body and collecting a response signal from the subject;
a light irradiator attached to the probe body and irradiating an optical signal; and
an etched reflecting surface formed on the probe body on a path of the optical signal,
wherein the etched reflecting surface changes the course of the optical signal from the light irradiator by reflecting the optical signal to a direction into which the electrode faces,
wherein a seating groove is formed on the probe body along a length direction of the probe body, the light irradiator is seated in the seating groove, the seating groove is provided with a slant surface facing an end portion of the light irradiator from which the optical signal is output, and the reflecting surface is the slant surface.

2. The optical stimulation probe according to claim 1, wherein the electrode is formed on a side portion of the probe body such that the direction the electrode faces is perpendicular to a length direction of the probe body, and the optical signal reflected by the reflecting surface travels along a direction perpendicular to the length direction of the probe body, such that the direction where the electrode faces and the direction along which the reflected optical signal travels are parallel to each other.

3. The optical stimulation probe according to claim 1, wherein the probe body is formed of silicon, and the seating groove is formed by wet etching.

4. The optical stimulation probe according to claim 3, wherein the probe body is formed from a silicon wafer having a [1, 0, 0] lattice structure.

5. The optical stimulation probe according to claim 1, wherein the light irradiator is an optical fiber or an optical waveguide transmitting the optical signal generated by an external light source.

* * * * *